United States Patent [19]

Park et al.

[11] Patent Number: 5,281,353
[45] Date of Patent: Jan. 25, 1994

[54] COMPOSITIONS AND METHODS FOR DISINFECTING/CLEANING OF LENSES AND FOR DESTROYING OXIDATIVE DISINFECTANTS

[75] Inventors: John Y. Park, Santa Ana; James N. Cook, Mission Viejo, both of Calif.

[73] Assignee: Allergan, Inc., Irvine, Calif.

[21] Appl. No.: 690,625

[22] Filed: Apr. 24, 1991

[51] Int. Cl.$^5$ ............................................. C11D 3/48
[52] U.S. Cl. ......................... 252/106; 252/174.12; 422/30; 424/94.4; 424/78.04
[58] Field of Search ................. 252/174.12, 106; 134/34; 422/30; 424/78.04, 94.4

[56] References Cited

U.S. PATENT DOCUMENTS

| | | | |
|---|---|---|---|
| Re. 32,672 | 5/1988 | Huth et al. | 252/95 |
| 3,482,025 | 12/1969 | Murakami et al. | 424/319 |
| 3,910,296 | 10/1975 | Karageozian et al. | 134/2 |
| 4,070,483 | 1/1978 | Lerman | 424/319 |
| 4,285,738 | 8/1981 | Ogata | 134/26 |
| 4,411,932 | 10/1983 | Kwan | 427/164 |
| 4,443,432 | 4/1984 | Garabedian et al. | 424/127 |
| 4,459,309 | 7/1984 | Chiou | 424/300 |
| 4,546,123 | 10/1985 | Schafer et al. | 523/106 |
| 4,550,022 | 10/1985 | Garabedian et al. | 424/127 |
| 4,559,343 | 12/1985 | Han et al. | 514/264 |
| 4,588,586 | 5/1986 | Kessler et al. | 424/94 |
| 4,609,493 | 9/1986 | Schafer | 252/546 |
| 4,613,379 | 9/1986 | Su et al. | 137/7 |
| 4,618,669 | 10/1986 | Decreu et al. | 252/105 |
| 4,670,178 | 6/1987 | Huth et al. | 252/95 |
| 4,690,773 | 9/1987 | Ogunbiyi et al. | 252/174.12 |
| 4,710,313 | 12/1987 | Miyajima et al. | 530/331 |
| 4,715,899 | 12/1987 | Chanda et al. | 134/26 |
| 4,734,475 | 3/1988 | Goldenberg et al. | 526/273 |
| 4,738,790 | 4/1988 | Miyajima et al. | 252/105 |
| 4,749,511 | 6/1988 | Lad et al. | 252/174.12 |
| 4,771,126 | 9/1988 | Hirotsuka et al. | 530/378 |
| 4,784,685 | 11/1988 | Meister | 71/106 |
| 4,837,021 | 6/1989 | Andermann et al. | 424/602 |
| 4,879,370 | 11/1989 | Meister | 530/331 |
| 4,880,601 | 11/1989 | Andermann et al. | 422/28 |
| 4,963,368 | 10/1990 | Antrim et al. | 424/498 |
| 5,145,644 | 9/1992 | Park et al. | 422/28 |

FOREIGN PATENT DOCUMENTS 1-180827 7/1989 Japan .

OTHER PUBLICATIONS

Bendazac Lysine In The Treatment Of Cataract, Brown et al, Clinical, Apr. 29, 1988.
Studies on the Mechanism of Action of Bendazac (AF 983), Silvestrini et al, Arzuema-Forsch(Drug Res.) Jahrgang 20—Nr. 2 (1970).
Abstract of Japanese Application JP-196378 Aug. 5, 1988.
Abstract of Japanese Application JP-011479 Jan. 19, 1989.

*Primary Examiner*—Gary P. Straub
*Assistant Examiner*—Timothy C. Vanoy
*Attorney, Agent, or Firm*—Frank J. Uxa

[57] ABSTRACT

Compositions and methods useful in destroying residual oxidative disinfectant, e.g., used to disinfect a contact lens, are disclosed. In one embodiment, the method comprises contacting an oxidative disinfectant-containing liquid medium with a material selected from glutathione, oxidized glutathione and mixtures thereof, and a co-factor selected from nicotinamide adenine dinucleotide phosphate, nicotinamide adenine dinucleotide and mixtures thereof in the presence of glutathione reductase in an amount effective to promote the oxidation of the co-factor.

17 Claims, No Drawings

COMPOSITIONS AND METHODS FOR DISINFECTING/CLEANING OF LENSES AND FOR DESTROYING OXIDATIVE DISINFECTANTS

BACKGROUND OF THE INVENTION

This invention relates to disinfecting and/or cleaning lenses, such as contact lenses. In particular, the invention relates to compositions and methods useful to quickly and effectively disinfect and/or clean lenses while reducing eye irritation caused by disinfecting the lenses.

Contact lenses should be periodically cleaned and disinfected by the user to prevent infection or other deleterious effects on ocular health which may be associated with contact lens wear. Currently, there are several different conventional systems and methods which enable the user to clean and disinfect their contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill the bacteria and fungi which may contaminate contact lenses. However, residual hydrogen peroxide on a disinfected contact lens may cause irritation, burning or trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens.

Associated with the problem of hydrogen peroxide destruction in contact lens disinfection systems are the problems of easy use and user compliance. To enhance user compliance and ease of use, several efforts have focused on one-step disinfection and hydrogen peroxide destruction. In this regard, various time release tablets containing a core tablet including a hydrogen peroxide destroying component, e.g., a hydrogen peroxide reducing agent, and having a delayed release coating on the core tablet have been suggested. The delayed release coating is necessary in these compositions because the hydrogen peroxide destroying components used provided very rapid, or kinetically fast, destruction of hydrogen peroxide. Thus, the delayed release coating allowed sufficient time for the hydrogen peroxide to disinfect the contact lens before the residual hydrogen peroxide was destroyed.

Such delayed release coatings are subject to various problems. First, the amount of time the release is delayed depends on the composition of the coating and the amount of the coating. In mass producing the coated tablets, each of these parameters may vary over a considerable range so that the final coating may not provide the intended delayed release. Thus, the lens may not be completely or effectively disinfected before the disinfectant is destroyed, or the disinfectant may still be present when the lens is put back into the eye, thus resulting in eye irritation or worse. In addition, the coating itself often becomes part of the disinfectant solution and may, by its nature, cause eye irritation.

There continues to be a need for a contact lens care system which rapidly and effectively disinfects, and preferably cleans, a contact lens so that the disinfected lens can be safely and comfortably worn.

SUMMARY OF THE INVENTION

New compositions and methods useful for disinfecting, and preferably cleaning, a lens, e.g., a contact lens, and for destroying residual oxidative disinfectants have been discovered. These compositions and methods take advantage of the catalytic redox system of the glutathione couple to destroy excess or residual oxidative disinfectant. By controlling the amounts of one or more components of the glutathione couple, for example, glutathione and/or oxidized glutathione and/or glutathione reductase, the rate of oxidative disinfectant destruction can be effectively controlled. No delayed release coating is required. For example, the amount of oxidized glutathione can be set so that a sufficient time is provided for the oxidative disinfectant to effectively disinfect the lens before the residual oxidative disinfectant is destroyed, enabling the lens wearer to wear the lens safely and comfortably. Further, the present system advantageously lends itself to a rapid and effective one step procedure for disinfecting, and preferably cleaning, a contact lens.

In one broad aspect, the present invention involves methods useful for disinfecting a lens, e.g., a contact lens, comprising contacting the lens to be disinfected with a composition. Such compositions comprise a liquid medium, preferably an aqueous liquid medium; an oxidative disinfectant, e.g., hydrogen peroxide, in an amount effective to disinfect a contact lens contacted with the composition; and an amount of the glutathione couple effective to destroy at least a portion, preferably substantially all, of the oxidative disinfectant present in the composition. The glutathione couple comprises a material selected from glutathione, hereinafter referred to as GSH, oxidized glutathione, hereinafter referred to as GSSG, and mixtures thereof; a co-factor selected from nicotinamide adenine dinucleotide phosphate, hereinafter referred to as NADPH, nicotinamide adenine dinucleotide, hereinafter referred to as NADH, and mixtures thereof; and glutathione reductase in an amount effective to promote the oxidation of the co-factor. The amount or amounts of one or more of the components of the glutathione couple present in the compositions are preferably effective to control the rate at which the oxidative disinfectant is destroyed.

In another broad aspect, the present invention is directed to compositions comprising GSSG; a co-factor selected from NADPH, NADH and mixtures thereof; and glutathione reductase in an amount effective when the composition is released into a liquid medium to promote the oxidation of the co-factor. In one embodiment, the compositions further comprise an oxidative disinfectant precursor. The compositions may further comprise at least one cleaning enzyme which when released into a liquid medium is capable of removing debris from a contact lens in the liquid medium. Thus, the present invention can provide for both oxidative disinfecting and enzymatic cleaning of a contact lens, with effective destruction of the residual oxidative disinfectant, all in a one step procedure.

DETAILED DESCRIPTION OF THE INVENTION

The present invention is of value where oxidative disinfectants are used to disinfect all types of lenses, e.g., contact lenses, which are benefited by periodical disinfecting. Such lenses, e.g., conventional contact lenses, in particular soft contact lenses, may be made of any suitable material or combination of materials and may have any suitable configuration not substantially deleteriously affected by the oxidative disinfectant employed, the present compositions or the present methods.

In one embodiment, the present invention involves a method for disinfecting a lens, in particular a contact lens. This method comprises contacting the lens to be disinfected with a composition comprising a liquid medium, preferably an aqueous liquid medium, an oxidative disinfectant in an amount effective to disinfect a contact lens contacted with, e.g., submerged in, the composition, a material selected from GSH, GSSG and mixtures thereof, a co-factor selected from NADPH, NADH and mixtures thereof, and glutathione reductase in an amount effective to promote the oxidation of the co-factor.

In the present invention, the redox system of the glutathione couple is used to destroy oxidative disinfectant, for example, residual oxidative disinfectant remaining after a contact lens has been effectively disinfected. By controlling the amount or amounts of one or more of the components of this couple, the rate at which the oxidative disinfectant is destroyed is controlled. Thus, for example, the amount of GSSG initially employed can be set so that sufficient time is provided to allow the oxidative disinfectant to perform its disinfecting function, e.g., to effectively disinfect a contact lens, before the oxidative disinfectant is substantially completely destroyed. Although the components of the glutathione couple can be released into the liquid medium at the same time as the active oxidative disinfectant, the oxidative disinfectant is present in an effective disinfecting amount for a sufficient period of time to perform its desired disinfecting function before the action of the glutathione couple destroys substantially all of the residual oxidative disinfectant. Thus, no delayed release coatings are required to prevent the immediate release of the components of the glutathione couple into the liquid medium containing the oxidative disinfectant. The destruction of the oxidative disinfectant is preferably kinematically controlled.

Thus, in one embodiment, the present invention involves a composition comprising the components of the glutathione couple together with a oxidative disinfectant precursor. This composition is preferably structured to release the couple components and the oxidative disinfectant precursor into a liquid medium at substantially the same time.

The components of the glutathione couple include a material selected from GSH, GSSG and mixtures thereof; a co-factor selected from NADPH, NADH and mixtures thereof; and glutathione reductase.

In one embodiment, the amount or amounts of GSH and/or GSSG, preferably GSSG, are selected to control the rate at which the oxidative disinfectant is destroyed, e.g., chemically reduced. Because of the cyclic redox nature of the oxidative disinfectant destruction, the amount of GSH and/or GSSG need not be stoichiometrically equal to the amount of oxidative disinfectant to be destroyed. It is preferred to use GSSG to control the rate of oxidative disinfectant destruction since GSH is quite a strong reducing agent and, thus, very quickly reduces the oxidative disinfectant, in particular hydrogen peroxide. On the other hand, GSSG interacts with the co-factor and the glutathione reductase to produce oxidized co-factor and GSH. This interaction involves a redox equilibrium and controls the amount of GSH produced by the glutathione couple and, in turn, controls the rate of oxidative disinfectant destruction. All other things being equal, the more GSSG (or GSH) present, the faster the rate of oxidative disinfectant destruction. Thus, the amount of GSSG (or GSH) chosen is preferably such as to provide sufficient time for the oxidative disinfectant to perform its destroying function and to substantially completely destroy the residual oxidative disinfectant within a reasonable time after this disinfecting function is accomplished.

The amount of GSSG (or GSH) used in the present compositions depends on a multitude of factors, for example, the specific oxidative disinfectant and amount thereof used, the specific disinfecting function to be accomplished, the length of time needed to accomplish this disinfecting function, and the length of time after the disinfecting function is accomplished before the residual oxidative disinfectant is to be destroyed. For example, if a contact lens is to be effectively disinfected using hydrogen peroxide as the oxidative disinfectant and the residual hydrogen peroxide is to be completely destroyed within 12 hours after the contact lens is first contacted with the hydrogen peroxide and components of the glutathione couple, the amount of GSSG present preferably is in the range of about 1% to about 50% of the stoichiometric amount, based on GSH, needed to reduce all the hydrogen peroxide present.

The amount of the co-factor included is preferably equal to at least the amount, in moles, of the oxidative disinfectant to be destroyed by the glutathione couple. Often for every mole of oxidative disinfectant destroyed, one mole of the co-factor is oxidized. Excesses of co-factor, i.e., amounts of co-factor in excess of the amount needed to provide for complete destruction of the oxidative disinfectant, are more preferably present so as to facilitate the functioning of the glutathione couple in destroying the oxidative disinfectant. Very large excesses, for example, more than about 500% of the amount needed for complete destruction of the oxidation disinfectant, of the co-factor are to be avoided as being unnecessary and wasteful.

The glutathione reductase is present in a catalytically effective amount, i.e., in an amount effective to promote the oxidation of the co-factor, e.g., by GSSG. The amount of glutathione reductase is preferably set so that the liquid medium containing the oxidative disinfectant to be destroyed contains about 1 ppm to about 100 ppm by weight of glutathione reductase. If desired, the amount of glutathione reductase employed can be used or set to control the rate of oxidative disinfectant destruction. All other things being equal, the more glutathione reductase present, the faster the rate of oxidative disinfectant destruction.

The composition used in disinfecting a contact lens in the present invention includes a disinfecting amount of oxidative disinfectant. Preferably, a disinfecting amount of oxidative disinfectant means such amount as will reduce the microbial burden by one log in three hours. More preferably, the oxidative disinfectant concentration is such that the microbial load is reduced by one log order in one hour. Still more preferred are those oxidative disinfectant concentrations which reduce the microbial load by one log unit in 10 minutes or less.

Any suitable oxidative disinfectant can be employed in the present invention provided it has no substantial detrimental effect on the present system and can be reduced by GSH. Examples of such useful oxidative disinfectants include hydrogen peroxide, chlorine dioxide, $ClO_2^{31}$ (chlorite ion) and mixtures thereof. One or more precursors of an oxidative disinfectant may be employed, provided that such precursors act to provide the desired active oxidative disinfectant as needed, e.g., to effectively disinfect a contact lens. The amount of oxidative disinfectant employed is preferably effective to disinfect a contact lens contacted with, e.g., submersed in, an oxidative disinfectant-containing liquid medium. Excesses of oxidative disinfectant, i.e., amounts of oxidative disinfectant greater than that needed to achieve the desired disinfecting, for example, of a contact lens, may be employed, for example, to increase the rate of disinfecting. Very large excesses of oxidative disinfectant are to be avoided as unnecessary and wasteful. Also, the more oxidative disinfectant used, the more residual oxidative disinfectant which is to be destroyed.

Particularly useful forms of oxidative disinfectant are aqueous hydrogen peroxide solutions, preferably containing about 0.5% to about 6% (w/v) of hydrogen peroxide, which are known to be effective disinfecting solutions for contact lenses. Such solutions are effective at killing bacteria and fungi which may be found on contact lenses.

A particularly useful embodiment of the present invention involves a solid composition comprising solid oxidative disinfectant precursor and solid glutathione couple components. The solid oxidative disinfectant precursor is capable of forming oxidative disinfectant in an amount effective to disinfect a contact lens contacted with a liquid medium which is combined with the composition. The solid glutathione couple components are present in an amount effective to destroy all the oxidative disinfectant present in the liquid medium. Thus, this composition, for example, in the form of a tablet, pill, capsule, mass of particles and the like, may be combined with, e.g., placed into a liquid medium, such as described elsewhere herein, preferably at or about the same time the lens to be disinfected is first contacted with the liquid medium. The lens is effectively disinfected and the residual oxidative disinfectant is destroyed.

Among the useful hydrogen peroxide precursors are per-acids and per-acid salts, such as ophthalmically acceptable perborates, percarbonates, percarboxylic acids, salts of percarboxylic acids; urea peroxide; and the like and mixtures thereof. Alkali and alkaline earth metal, in particular sodium and potassium, persalts are preferred if a persalt is to be used as the hydrogen peroxide precursor.

In one embodiment, the hydrogen peroxide precursor includes at least one enzyme capable of forming hydrogen peroxide in the liquid medium and at least one host material on which the enzyme acts to form hydrogen peroxide. Any suitable hydrogen peroxide producing enzyme may be employed provided that such enzyme or enzymes have no substantial detrimental effect on the present system, on the lens to be disinfected or on the wearer of the disinfected lens. Among the hydrogen peroxide-producing enzymes useful in the present invention are the following:

Aryl alcohol oxidase
L. Gluconolactone oxidase
Galactose oxidase
Aldehyde oxidase
Glycolate oxidase
Lactate oxidase
Glucose oxidase
Hexose oxidase
Xanthine oxidase
Pyrubate oxidase
Oxalate oxidase
Dihydro-orotate dehydrogenase
L-Amino acid oxidase
D-Amino acid oxidase
Mono Amine oxidase
Pyridoxamine phosphate oxidase
Diamine oxidase histaminase
Sarcosine oxidase
N-methyl-amino acid oxidase
Spermine oxidase
Nitroethane oxidase
Sulphite oxidase and mixtures thereof. The host material or materials to be utilized, of course, depends on the specific hydrogen peroxide-producing enzyme being utilized. Also, such host material should have no substantial detrimental effect on the present system, on the lens being disinfected or on the wearer of the disinfected lens.

One particularly useful hydrogen peroxide producing enzyme is glucose oxidase. When such enzyme is employed, the preferred host material is glucose.

In general, the chlorine dioxide precursors useful in the present invention are those which form or produce chlorine dioxide in a liquid medium, preferably a liquid aqueous medium, in response to the presence of the lens to be disinfected and/or one or more other factors. For example, such chlorine dioxide precursors may form or produce chlorine dioxide in the presence of certain metal-containing components or in a reduced pH environment.

Among the preferred chlorine dioxide precursors useful in the present invention is stabilized chlorine dioxide. The term "stabilized chlorine dioxide" as used herein means one or more chlorine dioxide-containing complexes and/or one or more chlorite-containing components and/or one or more other entities capable of forming chlorine dioxide in a liquid medium in response to the presence of the lens to be disinfected and/or one or more other factors. In addition, the chlorite-containing components may be effective as oxidative disinfectant precursors even without producing chlorine dioxide. Thus, chlorite ions, i.e., $ClO_2^-$ ions, can act as an effective oxidative disinfectant in the present invention.

Examples of such chlorite-containing components include metal chlorites, and in particular alkali metal and alkaline earth metal chlorites. A specific example of a chlorite-containing component which is useful as oxidative disinfectant precursor is technical grade sodium chlorite.

Among the preferred chlorine dioxide-containing complexes are complexes of chlorine dioxide with carbonate, chlorine dioxide with bicarbonate and mixtures thereof. The exact chemical composition of many of the chlorine dioxide precursors, e.g., stabilized chlorine dioxide, and in particular the chlorine dioxide complexes, is not completely understood. The manufacture or production of certain chlorine dioxide precursors is described in McNicholas U.S. Pat. No. 3,728,447, which is hereby incorporated in its entirety by reference herein. Specific examples of useful chlorine dioxide precursor sources include products such as that sold under the trademark Dura Klor by Rio Linda Chemical Company, Inc., and that sold under the trademark Anthium Dioxide by International Dioxide, Inc. An especially useful chlorine dioxide precursor source is a product sold under the trademark Purogene by Bio-Cide International, Inc.

One method for generating chlorine dioxide in an aqueous medium comprises buffering the medium to a pH between about 6 and about 10, preferably about 7.5, and exposing a chlorine dioxide precursor to a transition metal for at least one minute. Such transition metal should also have no substantial detrimental effect on the lens to be disinfected. Because of their high degree of effectiveness, platinum group metals and mixtures thereof, and especially platinum, are particularly useful. The metal or metals may be present in the metallic form and/or in a combined form as part of an organic or inorganic compound or complex.

Chlorine dioxide can be generated from a chlorine dioxide precursor by virtue of a lower pH, such as a pH of about 6 or lower. Thus, at mildly acidic conditions, in particular at a pH of about 6 or less and especially in the range of about 3 to about 5, the production of chlorine dioxide is effected.

Any suitable acidic component may be employed to increase the acidity of the liquid medium containing at least one chlorine dioxide precursor sufficiently to effect formation of chlorine dioxide from such chlorine dioxide precursor, and preferably sufficiently to effect formation of lens disinfecting amounts of chlorine dioxide from the chlorine dioxide precursor. Such acidic components should also have no substantial detrimental effect on the lens to be disinfected.

After the disinfecting contacting, the disinfected lens is preferably contacted with a liquid medium having reduced acidity relative to the liquid medium used in the disinfecting contacting, particularly if the disinfecting contacting occurred at a pH significantly less than 6. For example, the acidity of the liquid medium used in the disinfecting contacting can be reduced by adding an acidity adjusting component, for example, a basic component, a buffer component or mixture thereof, which have no substantial detrimental effect on the lens, to the liquid medium. In any event, after the disinfecting contacting, the disinfected lens is preferably present in a liquid aqueous medium which preferably has a pH in the range of about 6.0 or about 6.5 to about 8, and more preferably about 7.5. Such pH ranges are substantially consistent with the normal physiological pH for humans. Thus, after disinfecting, and destruction of the residual chlorine dioxide by the glutathione couple, the disinfected lens may be placed directly in the eye. Alternately, a simple saline rinse of the disinfected lens may be employed before placing the lens in the eye. This is in contrast to other systems which require elaborate neutralization procedures before the lens is suitable for placement in the eye.

The oxidative disinfectant precursor may be included in a liquid medium at a predetermined concentration, e.g., a concentration chosen to provide a disinfecting amount of the oxidative disinfectant as needed. If chlorine dioxide and/or $ClO_2^-$ ions are to be used as the oxidative disinfectant, the liquid medium preferably has sufficient oxidative disinfectant precursor so as to have a potential of producing chlorine dioxide and/or $ClO_2^-$ ions in the range of about 0.002% to about 3% by weight, based on the total weight of the liquid medium including the oxidative disinfectant precursor or precursors.

The liquid medium used is selected to have no substantial detrimental effect on the lens being treated and to allow, and preferably to even facilitate, the present lens treatment or treatments. The liquid medium is preferably aqueous-based. A particularly useful aqueous liquid medium is that derived from saline, such as a conventional saline solution. In the event hydrogen peroxide is used as the disinfectant, it is preferred that the aqueous liquid medium have a pH in the range of about 3 to about 9, more preferably about 6 to about 8 during the disinfecting contacting. The liquid medium, e.g., aqueous liquid medium, preferably includes a buffer which is present in an amount effective to maintain the pH of the liquid medium in the desired range. This buffer may be present in the liquid medium and/or may be introduced into the liquid medium, either separately or in combination with one or more of the other presently useful components. Among the suitable buffers or buffering agents which may be employed are those which are conventionally used in contact lens care products. Examples of useful buffers include those with carbonate functionalities, bicarbonate functionalities, phosphate functionalities, borate functionalities, and the like and mixtures thereof. The buffers may be alkali metal and alkaline earth metal salts, in particular sodium and potassium.

In one embodiment, the components of the glutathione couple are included in a solid composition, such as a tablet, capsule, one or more solid particles and the like, which is preferably introduced into liquid medium about the same time as the lens to be disinfected is introduced into the liquid medium.

The components of the glutathione couple, for example, in the present solid compositions, may be combined with one or more other components. Such other components may include, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here.

In a particularly useful embodiment, the present solid compositions further include at least one enzyme, i.e., cleaning enzyme, effective to remove debris from a contact lens. In this embodiment, the oxidative disinfectant preferably is to be hydrogen peroxide. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et. al. U.S. Pat. No. 32,672 Karageozian et al U.S. Pat. No. 3,910,296 are useful in the present invention. These patents are incorporated in their entirety by reference herein. Among the useful enzymes are those selected from proteolytic enzymes, lipases and mixtures thereof.

Preferred proteolytic enzymes are those which are substantially free of sulfhydryl groups or disulfide bonds, whose presence may react with the active oxygen in the HPLM to the detriment of the activity of the enzyme. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Aspergillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213–249 (1970) and Keay, L. and Moser, P. W., "Differentiation of Alkaline Proteases from Bacillus Species" Biochemical and Biophysical Research Comm., Vol 34, No. 5, pp 600–604, (1969).

The subtilisin enzymes are broken down into two sub-classes, subtilisin A and subtilisin B. In the subtilisin A grouping are enzymes derived from such species are *B. subtilis, B. licheniformis* and *B. pumilis*. Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

The present solid compositions which include such cleaning enzymes may be structured to release the enzyme, into the liquid medium which contacts the composition, at any time relative to the other component or components of the composition provided that the released enzyme is effective at the conditions present in the liquid medium to perform the cleaning function, as described herein. In one particularly useful embodiment, the cleaning enzyme is released into the liquid medium at substantially the same time as the components of the glutathione couple are so released.

The present solid compositions may be produced using conventional and well known manufacturing, e.g., tableting techniques.

Using the present compositions to disinfect, and preferably clean, a contact lens may be accomplished by contacting the lens to be disinfected with the composition if the composition includes a liquid medium, or with a combination of the composition and a liquid medium, at conditions effective to effectively disinfect the lens.

In the event that a cleaning enzyme is present in the composition, the contact lens in the liquid medium is also effectively cleaned of such debris. This cleaning action can occur before the lens is disinfected, at the time the lens is being disinfected, or after the lens is disinfected.

The disinfecting contacting preferably occurs at a temperature to maintain the liquid medium substantially liquid. It is preferred that the contacting temperature be in the range of about 0° C. to about 100° C., and more preferably in the range of about 10° C. to about 60° C. and still more preferably in the rang of about 15° C. to about 30° C. Contacting at or about ambient temperature is very convenient and useful. The contacting preferably occurs for a time to substantially completely disinfect the lens being treated. Such contacting times can be in the range of about 1 minute to about 12 hours or more.

After such contacting, the liquid medium preferably includes substantially no residual hydrogen peroxide, and the disinfected lens can be removed from this liquid medium and placed directly into the eye for safe and comfortable wear. However, if the liquid medium includes one or more "cleaning" enzymes, it is preferred to rinse the disinfected lens, e.g., with saline, to free the lens of such enzyme prior to placing the disinfected lens into the eye.

The following non-limiting examples illustrate certain aspects of the present invention.

EXAMPLE 1

This example illustrates a lens cleaning/disinfecting embodiment of the present invention.

A protein-based debris laden contact lens is placed in a plastic container. 10 ml of a saline solution containing 0.1% (w/v) of $H_2O_2$ and 0.3% by weight of boric acid is added to the container. The pH of this solution is about 7.5.

A tablet is dropped into the solution in the container. This tablet includes 0.05 g of GSSG, 0.25 g of NADPH, 0.5 mg of glutathione reductase, and 0.4 mg of subtilisin A enzyme.

Upon being dropped into the solution, the tablet dissolves to release its components into the solution. The subtilisin A enzyme begins to attack and remove the protein-based debris on the lens. Substantially all of the protein-based debris is removed from the lens. In addition, the contact lens is effectively disinfected. The hydrogen peroxide in the solution is destroyed at a controlled rate so that three (3) hours after the contact lens is first introduced into the solution, it is removed from the solution, rinsed with physiological saline solution to remove the subtilisin A enzyme and placed in the wearer's eye. It is found that the contact lens is effectively disinfected and cleaned of protein-based debris and the solution is substantially hydrogen peroxide-free. The lens wearer experiences no discomfort or eye irritation from wearing the disinfected and cleaned contact lens.

EXAMPLE 2

Example 1 is repeated except that the saline solution contains no hydrogen peroxide, and the tablet contains 200 mg of glucose and 10 mg of glucose oxidase.

Three (3) hours after the contact lens is first introduced into the solution it is removed from the solution, rinsed with physiological saline solution to remove the subtilisin A enzyme and placed in the wearer's eye. It is found that the contact lens is effectively disinfected and cleaned of protein-based debris and the solution is substantially hydrogen peroxide-free. The lens wearer experiences no discomfort or eye irritation from wearing the disinfected and cleaned contact lens.

EXAMPLE 3

Example 1 is repeated except that the saline solution contains no hydrogen peroxide, and the tablet used includes 50 mg of sodium perborate.

Three hours after the contact lens is first introduced into the solution it is removed from the solution, rinsed with physiological saline solution to remove the subtilisin A enzyme and placed in the wearer's eye. It is found that the contact lens is effectively disinfected and cleaned of protein-based debris. The lens wearer experiences no discomfort or eye irritation from wearing the disinfected and cleaned contact lens.

EXAMPLE 4

Example 1 is repeated except that the solution includes 0.018% by weight of a stabilized chlorine dioxide product sold by Bio-Cide International, Inc. under the trademark Purogene. This solution includes no $H_2O_2$ or boric acid. The tablet also includes sufficient acetic acid to provide the solution with a pH of about 6.0. No subtilisin A enzyme is included in the tablet.

Three hours after the contact lens is first introduced into the solution it is removed from the solution and placed in the wearer's eye. It is found that the contact lens is effectively disinfected and the solution is substantially chlorine dioxide-free. The lens wearer experiences no discomfort or eye irritation from wearing the disinfected contact lens.

EXAMPLE 5

Example 4 is repeated except that the solution includes no stabilized chlorine dioxide, and the tablet includes 0.0018 g of technical grade sodium chlorite.

Three hours after the contact lens is first introduced into the solution it is removed from the solution and placed in the wearer's eye. It is found that the contact lens is effectively disinfected and the solution is substantially chlorine dioxide- and chlorite ion-free. The lens wearer experiences no discomfort or eye irritation from wearing the disinfected contact lens.

While this invention has been described with respect to various specific examples and embodiments, it is to be understood that the invention is not limited thereto and that it can be variously practiced within the scope of the following claims.

What is claimed is:

1. A composition comprising:
    oxidized glutathione; a co-factor selected from the group consisting of nicotinamide adenine dinucleotide phosphate, nicotinamide adenine dinucleotide and mixtures thereof, glutathione reductase in an amount effective when said composition is released into an oxidative disinfectant-containing liquid medium to promote the oxidation of said co-factor; and at least one cleaning enzyme in an amount effective when released into a liquid medium to remove debris from a contact lens in the liquid medium.

2. The composition of claim 1 wherein said cleaning enzyme is present in an amount effective to substantially remove at least one type of debris from a debris laden contact lens in the liquid medium.

3. The composition of claim 1 which further comprises an oxidative disinfectant precursor.

4. The composition of claim 3 wherein said oxidative disinfectant precursor is selected from the group consisting of per-acids, per-acid salts, urea peroxide, stabilized chlorine dioxide, chlorites and mixtures thereof.

5. The composition of claim 3 wherein said oxidative disinfectant precursor is a precursor of hydrogen peroxide.

6. The composition of claim 5 wherein at least one of said oxidized glutathione and said glutathione reductase is present in an amount effective to control the rate at which said oxidative disinfectant is destroyed.

7. The composition of claim 3 which further comprises a liquid medium.

8. The composition of claim 3 wherein said oxidative disinfectant precursor includes at least one peroxide forming-enzyme capable of forming hydrogen peroxide in an aqueous liquid medium and at least one host material on which said peroxide forming-enzyme acts to form hydrogen peroxide.

9. The composition of claim 8 wherein said peroxide forming-enzyme is glucose oxidase and said host material is glucose.

10. The composition of claim 1 which further comprises a liquid medium and an oxidative disinfectant in an amount effective to disinfect a contact lens contacted with said composition.

11. The composition of claim 1 wherein said glutathione reductase is present in an amount effective when said composition is released into an oxidative disinfectant-containing liquid medium to interact with said oxidized glutathione and produce glutathione.

12. A composition comprising:
    oxidized glutathione; a co-factor selected from the group consisting of nicotinamide adenine dinucleotide phosphate, nicotinamide adenine dinucleotide and mixtures thereof; glutathione reductase in an amount effective when said composition is released into a liquid medium to promote the oxidation of said co-factor; and an oxidative disinfectant precursor.

13. The composition of claim 12 wherein said oxidative disinfectant precursor is selected from the group consisting of per-acid, per-acids salts, urea peroxide, stabilized chlorine dioxide, chlorites and mixtures thereof.

14. The composition of claim 12 wherein said oxidative disinfectant precursor is a precursor of hydrogen peroxide.

15. The composition of claim 12 wherein said oxidative disinfectant precursor includes at least one peroxide forming-enzyme capable of forming hydrogen peroxide in an aqueous liquid medium and at least one host material on which said peroxide forming-enzyme acts to form hydrogen peroxide.

16. The composition of claim 15 wherein said peroxide forming-enzyme is glucose oxidase and said host material is glucose.

17. The composition of claim 12 wherein sad glutathione reductase is present in an amount effective when said composition is released into a liquid medium to interact with said oxidized glutathione and produce glutathione.

* * * * *

UNITED STATES PATENT AND TRADEMARK OFFICE
CERTIFICATE OF CORRECTION

PATENT NO. : 5,281,353
DATED : January 25, 1994
INVENTOR(S) : Park et al

It is certified that error appears in the above-indentified patent and that said Letters Patent is hereby corrected as shown below:

Column 12, line 57, claim 13; change "per-acid, per-acids salts" to --per-acids, per-acid salts--.

Signed and Sealed this

Twenty-fourth Day of March, 1998

Attest:

BRUCE LEHMAN

Attesting Officer

Commissioner of Patents and Trademarks